United States Patent [19]
Sidot et al.

[11] Patent Number: 5,750,775
[45] Date of Patent: May 12, 1998

[54] SODIUM ORTHOHYDROXYMANDELATE/ PHENOL/WATER COMPLEX, PREPARATION PROCESS AND USE FOR ISOLATION OF SODIUM ORTHOHYDROXYMANDELATE

[75] Inventors: Christian Sidot, Compiegne; Michel Tarlier, Verberie, both of France

[73] Assignee: Societe Francaise Hoechst, Puteaux, France

[21] Appl. No.: 715,634

[22] Filed: Sep. 18, 1996

[30] Foreign Application Priority Data

Oct. 4, 1995 [FR] France ................................. 95 11658

[51] Int. Cl.$^6$ ................................................. C07C 59/48
[52] U.S. Cl. ....................................................... 562/470
[58] Field of Search ........................................... 562/470

[56] References Cited

FOREIGN PATENT DOCUMENTS

81/00404  2/1981  WIPO.

*Primary Examiner*—Paul J. Killos
*Attorney, Agent, or Firm*—Browdy and Neimark

[57] ABSTRACT

A crystallized sodium orthohydroxymandelate-phenol-water complex, its preparation process in which phenol ($P_2$) is introduced into an aqueous solution S at a pH comprised between 7 and 9.5 in order to obtain the expected product which is crystallized, the aqueous solution S being such as that resulting from the reaction of phenol ($P_1$) with glyoxylic acid in the presence of a tertiary amine and of a trivalent cation, then treatment using a solution of an alkaline hydroxide, use of this complex for the preparation of sodium orthohydroxymandelate (NaOHM), preparation process for the latter from the starting complex.

20 Claims, No Drawings

SODIUM ORTHOHYDROXYMANDELATE/ PHENOL/WATER COMPLEX, PREPARATION PROCESS AND USE FOR ISOLATION OF SODIUM ORTHOHYDROXYMANDELATE

The subject of the invention is the preparation of a crystallized sodium orthohydroxymandelate-phenol-water complex, its preparation process in crystallized form and the use of this complex for preparing sodium orthohydroxymandelate, either in crystallized form, or in the form of a solution with a high degree of purity.

The preparation of orthohydromandelic acid (OHMA) or of its sodium salt (NaOHM) in a sufficiently pure and easily manipulable form has not been able to be achieved on an industrial level.

Howe, R., Rao B. S. and Heynecker H. (J. Chem. Soc. (1967), 2510–2514) obtained orthohydroxymandelic acid in the form of a viscous gum from the reduction of 2-hydroxy-α-oxobenzeneacetic acid using hydrogen in an aqueous solution of sodium hydrogen carbonate in the presence of pre-reduced Adams catalyst.

According to this article, several attempts to isolate the ortho isomer of orthohydroxymandelic acid have failed. For example, it was proposed to treat salicylic aldehyde with hydrogen cyanide and to hydrolyze the resultant nitrile using a concentrated solution of hydrochloric acid. It was also proposed to reduce 2-hydroxy-α-oxobenzeneacetic acid using a sodium amalgam. Finally, it was proposed to diazotize the sodium salt of 2-aminomandelic acid and to heat the resultant diazonium compound with dilute sulphuric acid.

But, in all cases, the reaction products were always obtained in a viscous form with a low yield and according to processes which are difficult to implement.

At present, the known processes for obtaining orthohydroxymandelic acid or its alkaline salts start from the reaction of glyoxylic acid with phenol.

Hoefnagel A. J., Peters J. A., Van Bekkum H. (Recl. Trav. Chim. Pays-Bas (1988), 107 (3), 242–7) have shown that the condensation of glyoxylic acid with phenol could be catalyzed by certain metallic ions and that by operating in a dilute aqueous medium, at pH 5, at 100° C., in the presence of trivalent metallic cations such as aluminium, chromium, iron, it was possible to obtain high selectivities in ortho position. However, due on the one hand to a significant dilution which produces a low productivity and on the other hand to the obtaining of a high level of disubstituted products which leads to complex mixtures from which it is then difficult to isolate the desired orthohydroxymandelic acid, this process cannot be exploited on an industrial level.

Schouteeten A. and Christidis Y. have recently described in FR-A-2,687,143 a method allowing orthohydroxymandelic acid to be obtained with a yield of 86.5% by the condensation of glyoxylic acid with phenol in the presence of a tertiary amine, preferably tributylamine, and catalytic quantities of trivalent metallic cations, preferably $Al_2(SO_4)_3$, the by-products of this reaction being parahydroxymandelic acid and a disubstituted product in a very small quantity.

But in both above-mentioned cases, orthohydroxymandelic acid or its alkaline salts remain to be isolated in the pure state.

Recently Hoefnagel A. J., Peters J. A., Van Bekkum H. have described in WO-94,14746 a method for the separation of the ortho and para isomers from the alkaline salts of orthohydroxymandelic acid by selective extraction of aqueous mixtures. By carrying out an extraction of the mixture with a polar aprotic organic solvent, for example acetone, methylketone, tetrahydro-furan, ethyl acetate, it was found that the sodium salt of the ortho isomer was very soluble in these solvents. But such a process requires numerous extractions and evaporations and the repeated use of solvents, which makes the process difficult to carry out on an industrial scale, expensive and a source of pollution. Furthermore, none of the products obtained has the purity required for certain applications such as for example the synthesis of active ingredients for the pharmaceutical industry.

In an unexpected way, the Applicant has discovered that by starting from a sodium orthohydroxymandelate (NaOHM) - sodium parahydroxymandelate (NaPHM) mixture as described for example in FR-A-2,687,143, and by introducing phenol into this medium, an NaOHM-phenol-water complex was obtained, in the form of crystals.

This crystallized NaOHM-phenol-water complex allows the subsequent obtaining either of hydrated and crystallized NaOHM of high purity, or of an aqueous solution of NaOHM of high purity. This is particularly important for such a molecule which can be used as a synthesis intermediate in fine chemistry.

More particularly, the invention relates to a new sodium orthohydroxymandelate-phenol-water complex of formula (I):

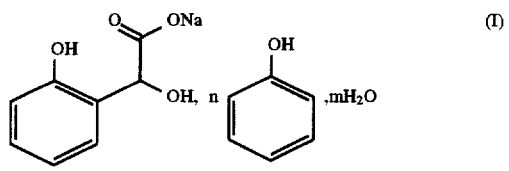

in which n is comprised between 0.8 and 1.2, preferably between 0.9 and 1.1 and in which m is comprised between 0.8 and 1.2. The term complex is understood as an addition complex, that is to say a compound whose molecule results from the juxtaposition of two or more others. The distinctive characteristic of the complex obtained is that it was able to be isolated in crystallized form.

The present invention also relates to a preparation process for the crystallized complex described above consisting of introducing phenol ($P_2$) into an aqueous solution S at a pH comprised between 7 and 9 in order to obtain the expected complex which is crystallized. The aqueous solution S is a solution such as one resulting from the reaction of phenol ($P_1$) with glyoxylic acid in the presence of a tertiary amine and of a trivalent cation, then treatment using a solution of an alkaline hydroxide, in particular as described in FR-A-2,687,143.

In a preferred manner, the aqueous solution S results from such a reaction, and is prepared under the following conditions:

The molar ratio of phenol ($P_1$) to glyoxylic acid is higher than 1, preferably higher than 4.

The molar ratio of tertiary amine to glyoxylic acid is comprised between 0.8 and 1.2, preferably between 0.9 and 1.1.

The trivalent cation is chosen from the group constituted by the trivalent cation of aluminium, chromium, iron, and preferably of aluminium.

The molar ratio of metallic cation to glyoxylic acid is comprised between 0.001 and 0.1, and preferably is equal to about 0.05.

The concentration by weight of the aqueous solution of glyoxylic acid used is about 50%.

The reaction temperature is higher than or equal to 50° C., preferably lower than 100° C.

This solution S will contain mainly sodium orthohydroxymandelate (NaOHM), sodium parahydroxymandelate (NaPHM) and optionally small quantities of hydroxybenzenediglycolic acids substituted in position -2,4 and in position -2,6 (HBDGA).

In order to form the desired crystallized complex, the molar ratio between the NaOHM contained in S and the phenol ($P_2$) which is introduced into S will be in particular of a value comprised between 0.5 and 1.5, preferably between 0.9 and 1.1. The pH of the reaction will be comprised between 7 and 9.

The crystallization of complex (I) will be carried out advantageously between 30° and 60° C., preferably between 40° and 50° C. After filtration and drying of the crystals, the expected complex (I) is obtained.

It has been possible to demonstrate that it is indeed a complex, in particular by its infrared spectrum which is different from the result of the addition of the individual spectra of NaOHM and of phenol in a mixture. It was also possible to demonstrate by thermogravimetric analysis that the water of the complex was indeed the constitutive water of the complex.

Also a subject of the invention is the use of the previously-mentioned crystallized complex for preparing sodium orthohydroxymandelate (NaOHM) of formula (II):

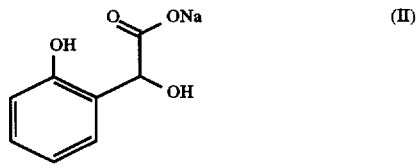

as well as a process for preparing sodium orthohydroxymandelate (NaOHM) of formula (II) from said complex.

The process is characterized by the fact that the above complex is treated using a solvent which does not solubilize the NaOHM but which solubilizes the phenol. More particularly a ketone will be used such as methylisobutylketone (MIBK) or acetone; preferably MIBK will be used. The product obtained after drying is almost anhydrous NaOHM in the form of a powder.

The present invention also relates to a preparation process for sodium orthohydroxymandelate (NaOHM) in aqueous solution starting from the previously-mentioned complex.

The process consists of treating complex (I) with a water-organic solvent S' mixture, S' being non-miscible with water and able to solubilize phenol. S' could be a ketone such as MIBK or an ether such as tertioamylmethylether (TAME), methyltertio-butylether (MTBE), diisopropylether (DIPE). TAME will preferably be used. Under the conditions described above very pure NaOHM was obtained, in particular with no trace of phenol.

The following examples are given for information only so that the invention may be better understood.

EXAMPLE 1

95 g of phenol (0.91 mole) in a 90% aqueous solution is added to a mixture of 1000 g of aqueous solution obtained according to the operating method described in Example 2 of FR-A-2,687,143 and containing essentially:

173 g (0.91 mole) of sodium orthohydroxymandelate (NaOHM)

34.2 g (0.18 mole) of sodium parahydroxymandelate (NaPHM)

5.7 g (0.02 mole) of sodium salts of hydroxybenzenediglycolic acids substituted in position -2,4 and in position -2,6 (NaHBDGA) the pH of which has been adjusted to 7. The whole is heated at 45° C. under agitation for 30 minutes, then cooled down slowly under gentle agitation. Crystallization starts at around 40° C.

The medium is left to return to ambient temperature for 12 hours then cooled down with an ice-bath to 5° C.

In this way a precipitate is then obtained which is filtered off then washed with 250 ml of bipermuted water at 5° C. In this way 224 g of moist product is recovered which, after drying in a drying oven under a reduced pressure of 50 mm of mercury at 50° C., produces 195 g of a creamy-white to orange solid product the melting point of which according to the capillary tube method is 105° C. The yield obtained is 71%.

Analysis of the final product by high performance liquid chromatography (HPLC) indicates the presence of a complex having the molar composition of 1 mole NaOHM - 0.92 mole phenol - 1.15 mole water. This analysis is confirmed by analysis of the complex carried out by acidimetry.

The infrared spectrum of the complex found is different from the spectrum resulting from the addition of the spectra of NaOHM and of phenol, which proves that a complex is indeed present and not a juxtaposition of three chemical entities.

The thermogravimetric analysis of the complex indicates that the water present is the constitutive water of the complex.

EXAMPLE 2

887 g of the isolated NaOHM-phenol-water complex, prepared according to Example 1, is suspended in 3000 cm$^3$ of methylisobutylketone (MIBK) and left for 12 hours under gentle agitation at ambient temperature. A precipitate is formed which is washed twice with 1000 cm$^3$ of MIBK.

In this way 575 g of moist product is recovered which is dried in a drying oven at 80° C. under reduced pressure for 12 hours, and which produces 536 g of dried product, that is a yield of 96% relative to the expected product.

Thermogravimetric analysis (TGA) and analysis of the water by the Karl Fischer method indicate that the product is almost anhydrous. The TGA allows it to be said that the product decomposes from 150° C. without melting being detected. The alkalimetry and acidimetry indicate a product with 99% purity.

The NMR and IR spectra are in accordance with the expected structure of the product, that is to say that of NaOHM.

EXAMPLE 3

2600 g of the isolated moist complex prepared according to Example 1 is suspended in a 10-litre reactor in 4300 g of bipermuted water at ambient temperature. Then three litres of tertioamylmethylether (TAME) is added and agitation is carried out for one hour at 25° C. All of the precipitate is solubilized. After agitation has stopped, two distinct phases are obtained.

After separation of these phases and washing of the aqueous phase three times with 1000 cm$^3$ of TAME and elimination of the TAME by concentration using a rotary evaporator, 5300 g of an aqueous phase is obtained, analysis of which by HPLC indicates a concentration of NaOHM of 22.4% by weight and the absence of phenol. The yield of the reaction is 99% and the product has a purity of 100%.

We claim:

1. A crystallized sodium orthohydroxymandelate-phenol-water complex.

2. A sodium orthohydroxymandelate-phenol-water complex according to claim 1, of formula (I):

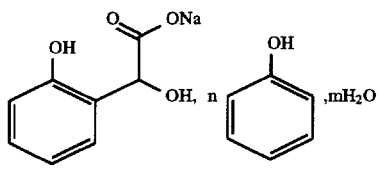

in which n is comprised between 0.8 and 1.2 and m is comprised between 0.8 and 1.2.

3. Process according to claim 2, characterized by the fact that the aqueous solution S is prepared under conditions such that:
- the molar ratio of phenol ($P_1$) to glyoxylic acid is higher than 1,
- the molar ratio of tertiary amine to glyoxylic acid is comprised between 0.8 and 1.2,
- the trivalent cation is a cation of aluminium, chromium or iron,
- the molar ratio of metallic cation to glyoxylic acid is comprised between 0.001 and 0.1,
- the glyoxylic acid is used in aqueous solution with a concentration by weight of about 50%,
- the reaction temperature is higher than or equal to 50° C.

4. Process one of claims 2 or 3, characterized by the fact that the aqueous solution S contains sodium orthohydroxymandelate (NaOHM), sodium parahydroxymandelate (NaPHM) and optionally hydroxybenzenediglycolic acids substituted in position −2,4 and in position −2,6 (HBDGA).

5. Process according to one of claims 3 to 4, characterized by the fact that the molar ratio of the NaOHM contained in the aqueous solution S to phenol ($P_2$) which is introduced into S is comprised between 0.5 and 1.5.

6. Process according to claim 5, characterized by the fact that the molar ratio of NaOHM contained in the aqueous solution S to phenol ($P_2$) entering into the reaction is comprised between 0.9 and 1.1.

7. Process according to one of claims 3 to 6, characterized by the fact that the pH of the aqueous solution S is adjusted to a value comprised between 7 and 9, before introduction of the phenol.

8. Preparation process for sodium orthohydroxymandelate (NaOHM) of formula (II) from the complex as defined in claim 1 for the preparation of sodium orthohydroxymandelate (NaOHM) of formula (II):

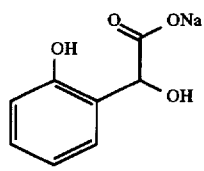

9. Preparation process for sodium orthohydroxymandelate (NaOHM) of formula (II) from the complex as defined in claim 1 or 2, characterized by the fact that said complex is treated using a solvent which solubilizes phenol but which does not solubilize NaOHM.

10. Process according to claim 9, characterized by the fact that the solvent is a ketone.

11. Preparation process for NaOHM of formula (II) in aqueous solution from the complex as defined in claim 1 or 2, characterized in that said complex is treated using a water/organic solvent S' mixture, S' being non-miscible with water and solubilizing phenol.

12. Process according to claim 11, characterized by the fact that S' is at least one of diisopropylether, methyltertiobutylether, methylisobutylketone and, tertioamylmethylether.

13. Process according to claim 3, characterized by the fact that the aqueous solution S contains sodium orthohydroxymandelate (NaOHM), sodium parahydroxymandelate (NaPHM) and optionally hydroxybenzenediglycolic acids substituted in position −2,4 and in position −2,6 (HBDGA).

14. Process according to claim 13, characterized by the fact that the molar ratio of the NaOHM contained in the aqueous solution S to phenol ($p_2$) which is introduced into S is comprised between 0.5 and 1.5.

15. Preparation process for sodium orthohydroxymandelate (NaOHM) of formula (II) from the complex as defined in claim 2, characterized by the fact that said complex is treated using a solvent which solubilizes phenol but which does not solubilize NaOHM.

16. Preparation process for NaOHM of formula (II) in aqueous solution from the complex as defined in claim 2, characterized in that said complex is treated using a water/organic solvent S' mixture, S' being non-miscible with water and solubilizing phenol.

17. Process according to claim 16, characterized by the fact that S' is at least one of diisopropylether, methyltertiobutylether, methylisobutylketone and, tertioamylmethylether.

18. A method of making sodium orthohydroxymandelate (NaOHM) of formula (II):

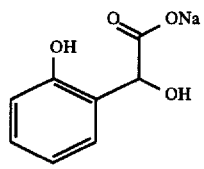

comprising isolating NaOHM from a complex according to claim 2.

19. A preparation process for preparing a complex as defined in claim 1, comprising:
- reacting phenol (P1) with glyoxylic acid in the presence of a tertiary amine and a trivalent cation, and adjusting the pH with an alkaline hydroxide to between 7 and 9 to obtain an aqueous solution(s); and
- adding phenol (P2) to said aqueous solution(s) and thereby obtaining said crystallized sodium orthohydroxymandelate-phenol-water complex.

20. A process according to claim 11 wherein said ketone is methylisobutylketone or acetone.

* * * * *